United States Patent [19]

Geysen

[11] Patent Number: 5,595,915
[45] Date of Patent: Jan. 21, 1997

[54] METHOD OF DETERMINING ANTIGENICALLY ACTIVE AMINO ACID SEQUENCES

[75] Inventor: Hendrik M. Geysen, Knexfield, Australia

[73] Assignees: Chiron Mimotopes Pty. Ltd, Victoria, Australia; Stichting Centraal Diergeneeskundig Instituut, Lelystad, Netherlands

[21] Appl. No.: 252,399

[22] Filed: Jun. 1, 1994

Related U.S. Application Data

[63] Continuation of Ser. No. 869,833, Apr. 19, 1992, abandoned, which is a continuation of Ser. No. 355,095, May 16, 1989, abandoned, which is a continuation of Ser. No. 680,338, filed as PCT/AU84/00039, Mar. 8, 1984, abandoned.

[30] Foreign Application Priority Data

Mar. 8, 1983 [AU] Australia ............................ PF8348/83

[51] Int. Cl.⁶ .................................................. G01N 33/53
[52] U.S. Cl. ........................ 436/518; 436/528; 436/531; 436/532; 436/543; 530/333; 530/334; 435/7.92
[58] Field of Search ........................ 436/501, 518, 436/528, 531, 532, 543, 89; 435/6, 7.92; 530/333, 334

*Primary Examiner*—Toni R. Scheiner
*Attorney, Agent, or Firm*—Sughrue, Mion, Zinn, Macpeak & Seas

[57] ABSTRACT

A method of detecting or determining a sequence of amino acids which is antigenically active within a known amino acid sequence of a protein or portion thereof comprises the steps of: synthesising a plurality of peptides, each of said peptides comprising a sequence of a plurality of amino acids which corresponds to a sequence within the known amino acid sequence, and the said peptides having overlapping amino acid sequences; contacting each of said peptides with antibody against the protein or portion of interest; and detecting or determining the presence or absence of an antigen-antibody reaction between each of said peptides and said antibody to indicate whether or not said peptide has antigenic activity.

11 Claims, 5 Drawing Sheets

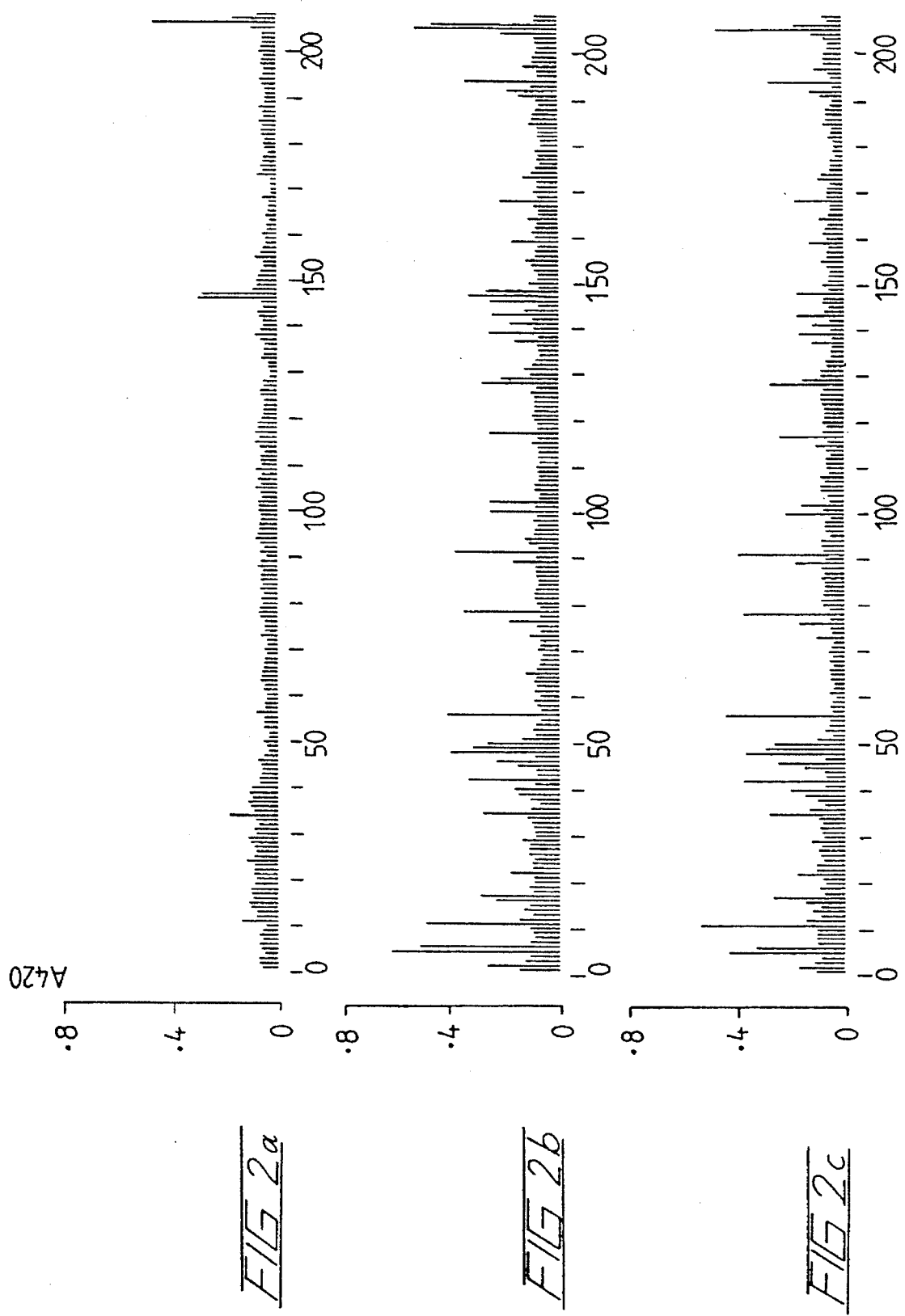

METHOD OF DETERMINING ANTIGENICALLY ACTIVE AMINO ACID SEQUENCES

This is a continuation of application Ser. No. 07/869833 filed 16 Apr. 1992, now abandoned, which is a continuation of Ser. No. 07/355095 filed 16 May 1989, now abandoned, which is a continuation of Ser. No. 06/680338 filed as PCT/AU84/00039, Mar. 8, 1984, now abandoned.

This invention relates to a method of detecting or determining antigenically active sequences of amino acids in a protein. The term "antigenically active" used throughout this specification is intended to denote any amino acid sequence which will combine specifically with an antibody, and includes sequences which also elicit or stimulate the production of antibodies (these latter sequences are also referred to as being "immunogenic").

As is already well known, an antigen is a macromolecule such as a protein which is usually foreign to a human or animal and which is capable of eliciting the formation of an antibody by the human or animal, the antibody being a protein synthesized by the human or animal in response to the presence of the macromolecule. The antibody has specific affinity for the macromolecule that elicited its synthesis, the specificity of the antibody being directed against one or more particular sites or amino acid sequences on the macromolecule usually referred to as the "antigenic determinant(s)".

It is a primary object of the present invention to detect or determine the sequence or sequences of amino acids which constitute the antigenic determinant(s) of a selected protein, for example, the antigen responsible for eliciting the antibodies which protect against a particular clinical disease such as foot and mouth disease or hepatitis.

According to the present invention there is provided a method of detecting or determining a sequence of amino acids which is antigenically active within a known amino acid sequence of a protein or portion thereof, the method comprising the steps of:

1. synthesising a plurality of peptides, each of said peptides comprising a sequence of a plurality of amino acids which corresponds to a sequence within the known amino acid sequence, and said peptides having overlapping amino acid sequences;

2. contacting each of said peptides with antibody against the protein or portion of interest; and 3. detecting or determining the presence or absence of an antigen-antibody reaction between each of said peptides and said antibody to indicate whether or not said peptide has antigenic activity.

As noted above, the peptides synthesized in accordance with this method have overlapping amino acid sequences, that is, one peptide is related to another peptide in that at least one amino acid is omitted from one end of the sequence of the other peptide and at least one amino acid added to the opposite end of the sequence, with the remaining amino acids being common to both sequences. The amino acids within these overlapping sequences are of course selected so that each sequence corresponds to a sequence within the known amino acid sequence of the protein or portion thereof, as previously described.

The method of the present invention is based upon the concept that a given antibody specifically recognises a sequence of amino acids which has the particular antigenic activity of interest, and that as a result a particular antigenic determinant can be ascertained by utilising this high degree of specificity of the antibody to identify the specific sequence of amino acids of the particular antigenic determinant from among all the possible combinations thereof.

Several recent publications relate to work aimed at identifying the sequence(s) of amino acids representing the active antigen or antigenic determinant of immunogenic proteins. By currently available methods, however, the identification of the active sequence(s) of amino acids within a protein molecule is a long and involved process. The present invention detects, the sequences of amino acids which are antigenically active by a screening process using peptides having overlapping sequences as described above.

It is believed that an antigenic determinant generally comprises a sequence of about six amino acids in length, and accordingly the sequences of amino acids which are prepared in accordance with the first step of the present invention are preferably sequences of six amino acids. It is to be understood, however, that the present invention is not restricted to sequences of six amino acids although by present indications sequences which are five units in length would seem to be too small to give an easily detected reaction in the subsequent screening procedure. Sequences of nine or more units in length are probably unnecessarily long and thus, such sequences are presently not preferred; however, they are encompassed within the broad, ambit of the present invention.

In performance of this invention, use is made of previous determination of the amino acid sequence of the protein or protein region believed to carry the antigenic determinant of interest. Amino acid sequences of a large number of proteins are already known and modern methods of sequencing, for example using recombinant DNA techniques, provide a rapid method of sequencing proteins for which the amino acid sequence is still unknown.

The importance of this invention lies in its ability to identify the antigenic determinant(s) of a protein as short amino acid sequences with unsurpassed ease. Furthermore, every continuous antigenic determinant of importance can be identified. This information is invaluable in the design of reagents with the necessary selectivity to be used in the diagnosis of clinical diseases in man and animals. A knowledge of the antigenic determinant associated with a particular infectious agent is also essential in the production of peptide vaccines which will confer protection against the disease without many of the deleterious side effects of conventional vaccines. The invention also can be used in the design of very specific therapeutic reagents against receptor sites in the body.

One example of the use of the above method in the determination of an antigenic determinant within a protein or portion of a protein is as follows:

1. Commencing with the known amino acid sequence of the protein or portion of interest, obtained for example from published data, take the order of the first six amino acids (assuming that all synthesized peptides in this example will be six amino acids long), starting either from the amino terminal end or from the carboxy terminal end, and designate this as "Sequence one". "Sequence two" is then the set of six amino acids in order starting at the second amino acid and proceeding up to and including the seventh amino acid. By extending this procedure of "dropping" one amino acid from one end and adding the next in the known sequence to the other end, the necessary amino acid sequences for all hexapeptides contained within the protein or portion of interest are obtained. The total number of such sequences will be five less than the actual number of amino acids making up the protein or portion of interest.

2. Each sequence determined as described above is then synthesized. Suitable methods include the well-known procedures for peptide synthesis commonly referred to as:

(a) solution phase methods; or
(b) solid phase methods; e.g. the Merrifield technique: Marglin, A. and Merrifield, R. B., Ann. Rev. Biochem. 39, 841–866 (1970).

Preferably, however, the synthesis of the amino acid sequences is effected by a solid phase method which comprises the use of a polymeric material such as polyethylene or polypropylene as the solid-phase carrier, onto which is graft polymerised a vinyl monomer containing at least one functional group to produce polymeric chains on the carrier. The functional groups of these polymeric chains are then reacted to provide primary or secondary amino groups of the chains, and these amino groups are then sequentially reacted with amino acid residues in appropriate order so as to build up a desired synthetic peptide. The carrier is preferably in the form of a solid polymer rod having a diameter of about 4 mm and a length of about 50 mm. A number of such rods can be held in a suitable holder in a 12×8 grid whose dimensions correspond to those of the standard plate used for enzyme-linked immunosorbent assays (ELISA).

3. Depending on the choice of procedure for the synthesis of each peptide, the peptide is either already attached to a suitable support at the completion of the synthesis procedure, or is coupled to a suitable solid support in preparation for the assay step.

4. The supports carrying the synthesized peptides are transferred to the wells of a microtitre plate or like apparatus, and each known sequence is then screened against known antibodies, using the usual methods to indicate the presence or absence of an antigen-antibody reaction in each well. Examples of these methods include enzyme linked immunosorbent assay (ELISA) and radio immunoassay (RIA). Suitable antibodies can either be purchased as commercially available antisera or prepared in a suitable host animal in accordance with well known procedures.

Preferably, a computer-based management program is used to aid in the organisation of the synthesis of the six-unit long amino acid sequences as described above. This can be used to achieve a record of the eventual peptide identity for each location in each microtitre plate, and in addition allows determination of the order of synthesis to be undertaken simultaneously on the basis of compatible conditions of reaction. Finally, such a management program can be used in conjunction with a program written for the final evaluation at the antibody screening stage.

As will be set out in greater detail in the Examples, the method outlined in the above steps has been used to ascertain antigenically active amino acid sequences of the foot and mouth disease virus (FMDV) protein VP1. Of course, the present invention can similarly be applied in determination of antigenic determinants of other virus proteins, such as Hepatitis B virus surface antigen, as well as any other protein for which the sequence is known.

BRIEF DESCRIPTION OF THE DRAWINGS

FIGS. 2a–2f show antigenic profiles for hexapeptide submits of the 213-amino acid sequence of VP1 (FMDV type $O_1$).

The well-known indirect ELISA technique is preferably used for final detection or determination of the presence or absence of an antigen-antibody reaction between the sequences of amino acids and the given antibody. The use of this assay necessitates the preparation of antisera directed against the antibody species to be used in the final testing, for example, anti-human IgG, anti-bovine IgG, and so on. Such preparations are then conjugated with an enzyme, such as horseradish peroxidase, to provide test reagents required for the final testing. Performance of the indirect ELISA assay is carried out by the techniques well known in this field.

Where the method of the present invention is performed in a screening test of the type described above, the results obtained with a particular antibody fall into one of the following categories:

(a) No positive reaction with any of the prepared amino acid sequences, i.e. complete negative.

(b) Reaction with a single amino acid sequence only. This result represents the ideal case.

(c) Reaction with a number of amino acid sequences. This observed result can be expected for one of two reasons: one, reaction with an antiserum containing a mixed antibody population, each antibody of which is reacting with a different antigenic site; or two, reaction with amino acid sequences which overlap the immunogenic site. In the first case, further testing will be required to determine the more useful antigenically active amino acid sequences.

It will, of course, be appreciated that once the sequence of amino acids which is antigenitally active in reacting with a given antibody has been detected or determined, this information can be used in various diagnostic applications, and in the production of vaccines. In fact, where the antigenically active sequence of amino acids corresponding to a particular clinical disease agent has been determined, this can lead to the production of a vaccine which will provide protection against that disease and which comprises one or more synthetically produced sequences of appropriate amino acids which will elicit the desired antibody response.

Further features of the present invention are illustrated by way of example only in the following Examples:

EXAMPLE 1

A. Preparation of hexapeptides

Figure 1:
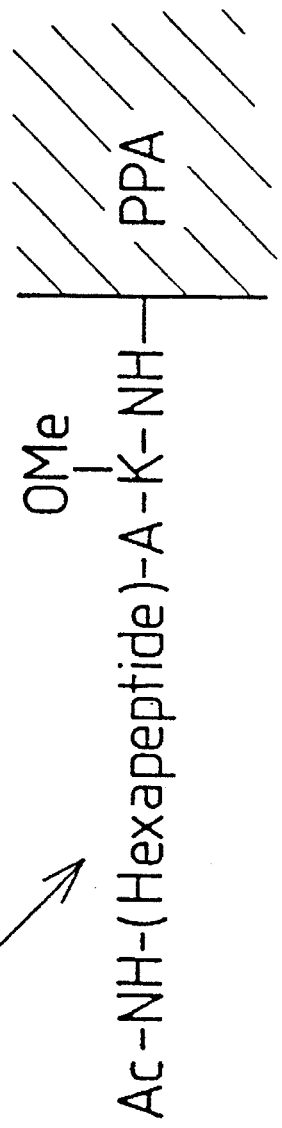
FIG. 1 illustrates synthesis of hexapeptide subunits of the 213-amino acid sequence of VP1 (FMDV type $O_1$) on a polyethylene support.
Figure 1:
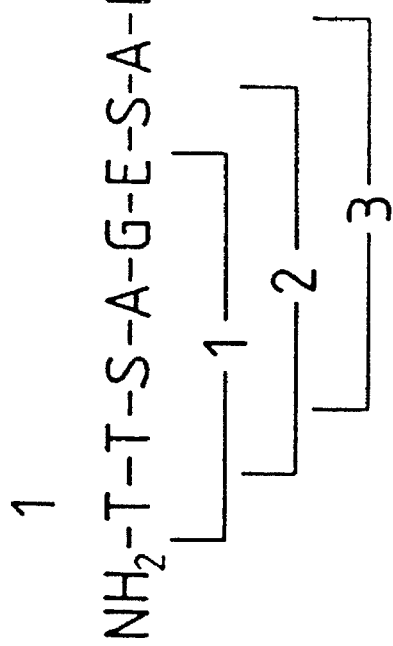
Figures 2D, 2E, 2F:
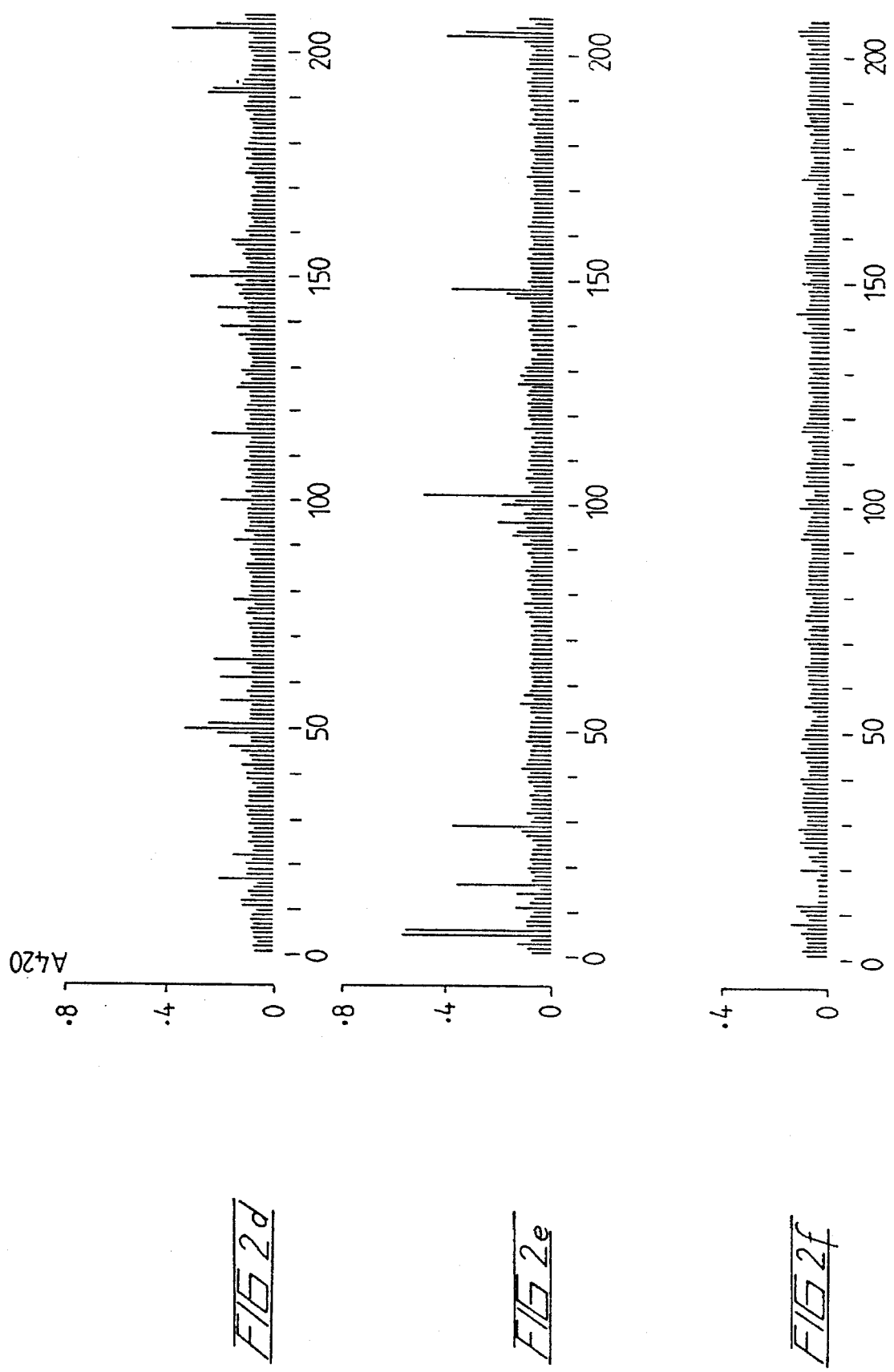

The 213-amino acid sequence of VP1 (FMDV, type $0_1$) as translated by Kurz, C. et al., Nucleic Acid Research 9, 1919–1931 (1981) was subdivided into all possible hexapeptide units, and each hexapeptide unit was synthesized on a polyethylene support in the same orientation, and with a 2-long amino acid spacer as illustrated in FIG. 1.

Polyethylene rods immersed in a 6% v/v aqueous solution of acrylic acid were γ-ray irradiated at a dose of 1 Mrad (see Muller-Schulte, D., Horster, F. A., Polymer Bulletin 7, 77–81 (1982)). Using conventional methods of solid-phase peptide chemistry (see Erickson, B. W., Merrifield, R. B. in "The Proteins", Vol. 2, 255–257, Academic Press, New York (1976); Meienhofer, J., in "Hormonal Proteins and Peptides", Vol. 2. 45–267, Academic Press, New York (1973)), $N^{\alpha}$-t-Butyloxycarbonyl-L-Lysine methyl ester was coupled to the polyethylene polyacrylic acid (PPA) via the N-amino group of the side-chain. This was followed by the coupling of Boc-Alanine, to complete a peptide-like spacer. Amino-substitution of the support was determined by reacting $NH_2$-Lysine(OMe)-PPA with $C^{14}$ labelled butyric acid, and was found to be 8–10 nmoles/rod.

Successive amino acids were added by conventional solid phase peptide synthesis as dictated by the sequence to be synthesized. At the completion of the final coupling reaction, and after removal of the t-butyloxycarbonyl (Boc) protecting group, the terminal amino group was acetylated with acetic anhydride in a dimethylformamide (DMF)/triethylamine mixture. All dicyclohexyl carbodiimide-mediated coupling reactions were carried out in DMF in the presence of N-hydroxy benzotriazole. The following side-chain protecting groups were used; O-benzyl for threonine, serine, aspartic acid, glutamic acid and tyrosine; carbobenzoxy for lysine; tosyl for arginine; 4-methyl benzyl for cysteine and 1-benzyloxycarbonylamido-2,2,2,-trifluoroethyl for histidine. Side-chain deprotection was achieved by treatment with borontris (trifluoracetate) in trifluoreacetic acid for 90 minutes at room temperature (see Pless, J., Bauer, W., Angewante Chemie 85, 142 (1973)). After hydrolysis in HCl/propionic acid, analysis of sequences included in the synthesis as controls confirmed that coupling at each stage had occurred. Before testing by ELISA, rod-coupled peptides were washed several times in phosphate buffered saline (PBS).

B. Testing of Hexapeptides

Antigenic profiles for the hexapeptides prepared as described in A. above are shown in FIGS. 2a–2f as vertical lines proportional to the ELISA extinction obtained, over the number giving the location within the VP1 sequence of the peptide N-terminal amino acid. Antisera used to produce the different profiles as shown, were as follows:

2a and 2b: two different anti-intact virus particle, type $O_1$;

2c: anti-intact virus particle, as used in (b), after absorption with purified complete virus, type $O_1$;

2d: anti-virus-subunit, type $O_1$;

2e: anti-VP1, type $O_1$ and

2f: anti-intact virus particle, type $C_1$.

The enzyme-linked immunosorbent assay was used to test each rod-coupled peptide (RCP) for reactivity with each of the defined antisera described above. RCPs were pre-coated with 10% horse serum, 10% ovalbumin and 1% Tween-80 in PBS, to block non-specific absorption of antibodies, for 1 hour at 37° C. Overnight incubation at 4° C. in antiserum diluted 1/40 in the preincubation mixture, was followed by 3 washes in 0.05% Tween-80/PBS. Reaction for 1 hour at 37° C. with the appropriate anti-rabbit IgG immunoglobulin coupled to horse radish peroxidase, diluted 1/50,000 in the preincubation mixture, was again followed by extensive washing in PBS/Tween to remove excess conjugate. The presence of antibody was detected by reaction for 45 min with a developing solution (40 mg orthophenylenediamine, 20 µl of hydrogen peroxide in 100 ml of phosphate buffer, pH 5.0), and the colour produced read in a Titertek Multiscan at 420 nm. After tests, peptides were washed three times at 37° C. in 8M urea containing 0.1% 2-mercaptoethanol and 0.1% sodium dodecyl sulphate, followed by several washes in PBS to remove all traces of bound antibody. The RCPs were then ready for further testing with different antisera.

Anti-intact virus particle sera were prepared by immunising rabbits with 50 µg of inactivated, purified virus in complete Freund's adjuvant. The animals were bled 3–4 weeks after the single vaccination. Anti-virus-subunit serum (rabbit) was prepared by immunizing 3 times, 3–4 weeks apart, with 10 µg of acid-disrupted purified virus, initially in complete Freund's and subsequently in incomplete Freund's adjuvant. The polypeptide VP1 was separated from. The mixture of proteins obtained from urea disrupted, purified virus, by iso-electric focusing. (see Barteling, S. J., Wagenaar, F., Gielkens, A. L. J., J. Gen. Virol. 62, 357–361 (1982).) After elution from the gel with 8M urea and dialysis against PBS, antiserum was raised as described for 12S above. Antiserum for scan 2c was that used for scan 2b, but after absorption with purified virus (1500 µg complete virus was incubated with 1 ml of serum for 72 hours at 4° C.), and all virus bound antibodies removed by centrifugation.

C. Identification of the virus particle-associated antigenic peptide

Of the four anti-intact virus particle sera tested, scans 2a and 2b show the extremes in the reactivity patterns found. Large quantitative differences in the response to an identical antigen preparation have been reported before, however, these scans highlight the variability possible in the antibody composition between sera. From an examination of scans 2a, 2b and 2c, antibody reactive with peptides numbers 146 and 147 are present in whole anti-intact virus sera, but absent after absorption with purified virus. These same antibodies are not observed in the anti-subunit sera, scan 2d, and only weakly present in the anti-VP1 sera, scan 2e. That some activity was found in the anti-VP1 sera, possibly accounts for the immunizing capacity, albeit weak, of the isolated protein. (see Kleid, D. G., et al., Science 214, 1125–1129 (1981).) It should be noted however that another anti-VP1 serum also tested, while retaining a strong activity in position number 148, showed nothing at positions numbers 146 and 147. The. superimposition of scan 2c on scan 2b (absorbed compared to non-absorbed) shows that in addition to the loss of activity to peptides numbers 146 and 147, a reduction in activity to peptides numbers 5, 6 and 206 also occurred. Of these, activity to numbers 5 and 6 was not found in all the anti-intact virus sera tested, whilst number 206 activity was invariably present.

From these results, it is concluded that of the sequences found to be reactive, the pair at numbers 146 and 147, that is the hexapeptides Gly-Asp-Leu-Gln-Val-Leu (G—D—L—Q—V—L) and Asp-Leu-Gln-Val-Leu-Ala (D—L—Q—V—L—A), constitute the principal loci, with a lesser contribution from the locus at number 206, consistent with the observations of others. However, with respect to the loci at numbers 146–7, we do not distinguish between the two possibilities; one, that the active element is five amino acids long, i.e. The sequence common to both Asp-Leu-Gtn-Val-Leu (D—L—Q—V—L); or two, that the active element is seven amino acids long, i.e. The combination of the two hexapeptides Gly-Asp-Leu-Gln-Val-Leu-Ala (G—D—L—Q—V—L—A).

EXAMPLE 2

A. Preparation of Hexapeptides

The 212 amino acid sequence of VP1 (FMDV type $A_{10}$ or $A_{61}$) as given by Bachrach, H. L., et al, Office International des Epizootics was subdivided into 207 hexapeptides. These hexapeptides were synthesised as described in Example 1 above with the exception that the side chain of arginine was protected by the p-methoxybenzene sulphonyl group.

B. Testing of Hexapeptides

Figures 3A, 3B:
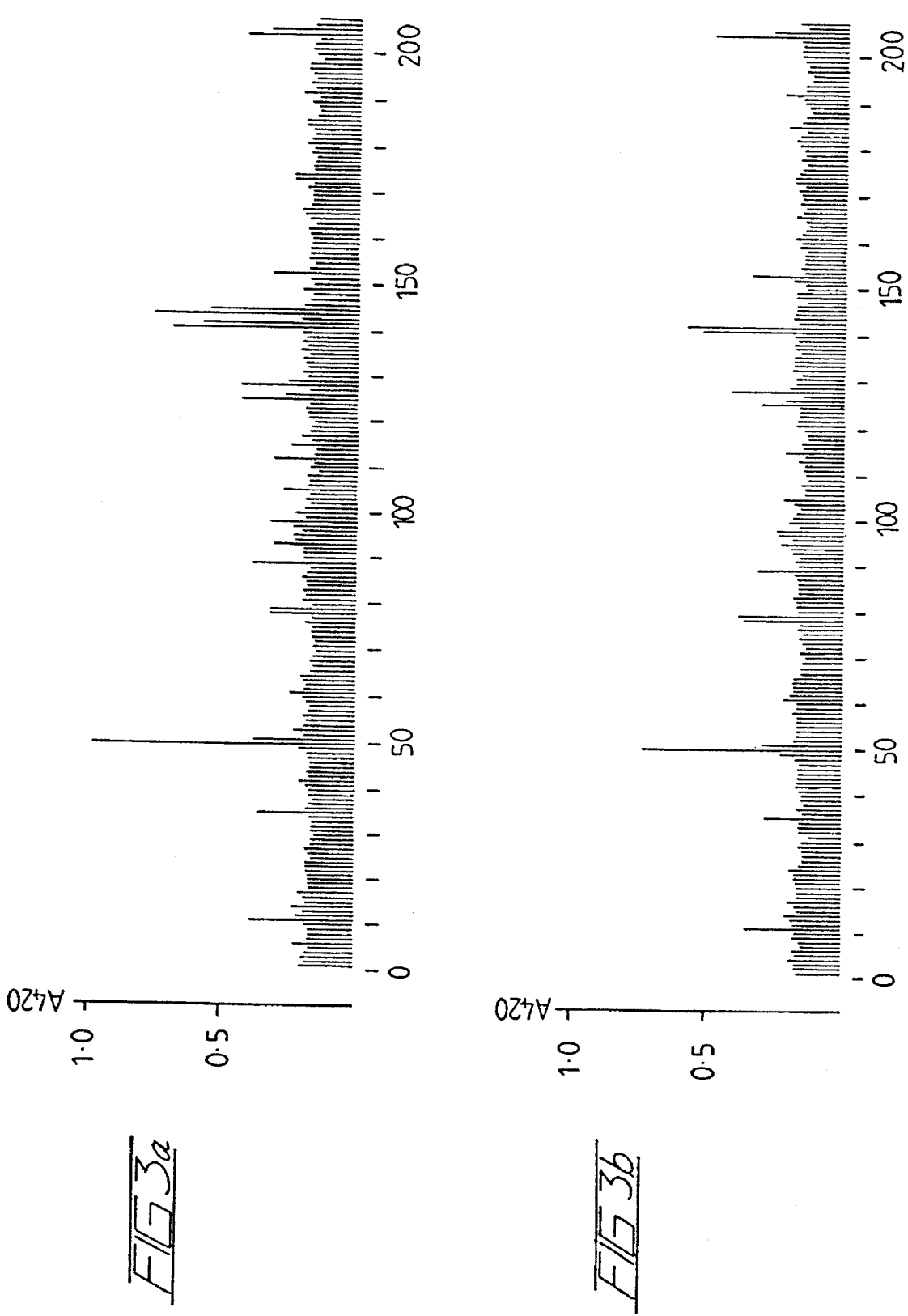
FIGS. 3a and 3b show antigenic profiles for hexapeptide subunits of the 212-amino acid sequence of VP1 (FMDV type $A_{10}$).

Antigenic profiles for the hexapeptides are shown in FIGS. 3a and 3b. The antisera used to produce the profiles were:

3a: anti-intact virus particle type $A_{10}$

3b: anti-intact virus particle as used in (a) after adsorption with purified complete FMDV type $A_{10}$.

The testing of the hexapeptide and preparation of the sera were essentially as described in Example 1.

C. Identification of virus-particle associated active element

By reasoning identical to that used in Example 1 it is concluded that the hexapeptides Gly-Asp-Leu-Gly-Ser-Ile (G—D—L—G—S—I) and Asp-Leu-Gly-Ser-Ile-Ala (D—L—G—S—I—A) are the principal loci for the antigenic determinant of the A-type of FMDV.

As in the case of FMD virus, type $O_1$, described in Example 1, we did not distinguish between these two sequences, and accordingly it is concluded that it is possible that the active sequence is five amino acids long, i.e. Asp-Leu-Gly-Ser-Ile (D—L—G—S—I), or that it is seven amino acids long, i.e. Gly-Asp-Leu-Gly-Ser-Ile-Ala (G—D—L—G—S—I—A).

EXAMPLE 3

A. Preparation of Hexapeptides

The 210 amino acid sequence of VP1 (FMDV type $C_1$) as given by Robertson, H. L., et al., Journal of Virology, 46, 311–316 (1983) was subdivided into 205 hexapeptides. These hexapeptides were synthesised as described in Example 2 above.

B. Testing of Hexapeptides

Figure 4A:
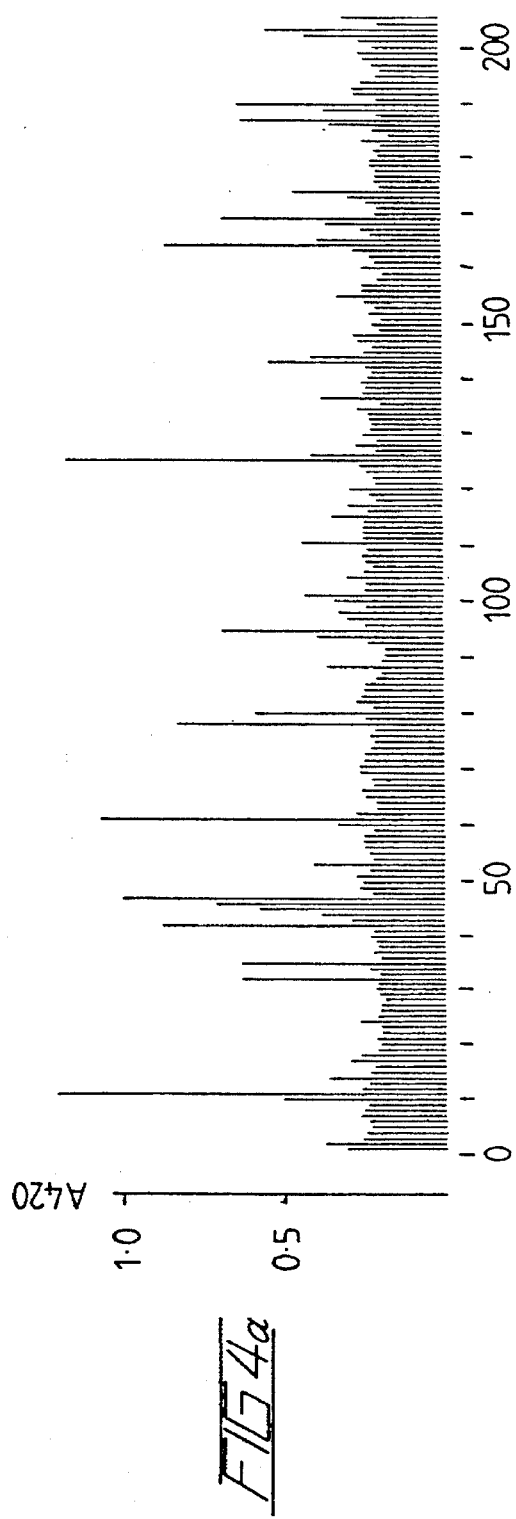
FIGS. 4a and 4b show antigenic profiles for hexapeptide subunits of the 210-amino acid sequence of VP1 (FMDV type $C_1$).
Figure 4B:
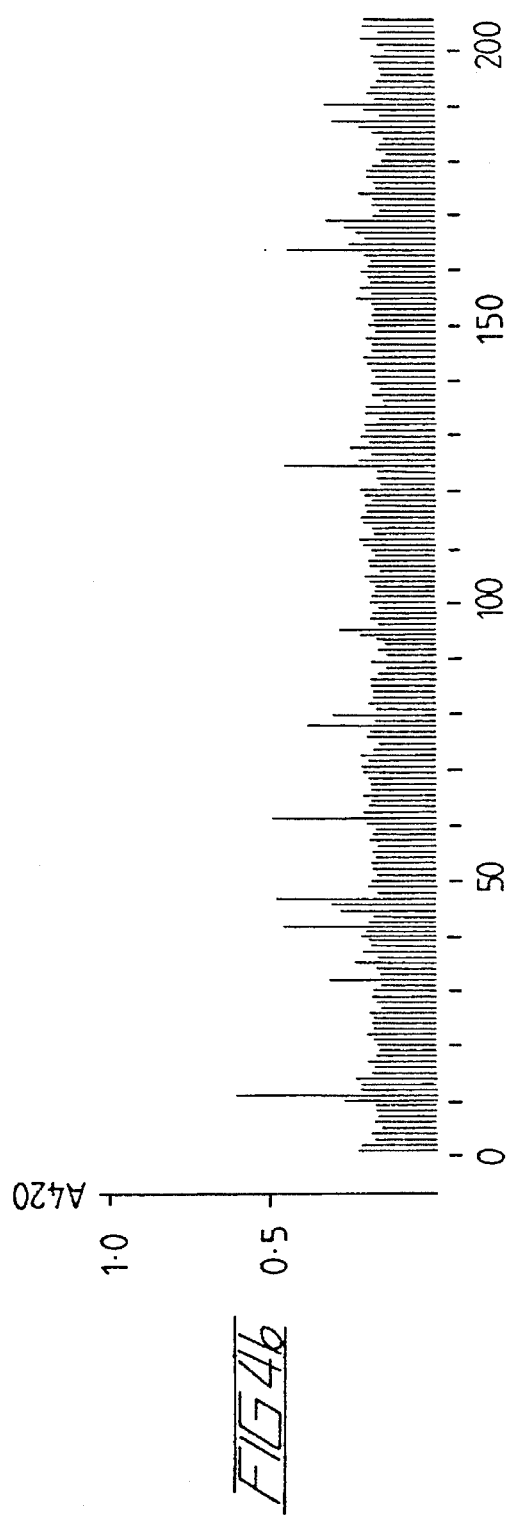

Antigenic profiles for the hexapeptides are shown in FIGS. 4a and 4b. The antisera used to produce the profiles were:

4a: anti-intact virus particle type $C_1$

4b: anti-intact virus particle as used in (a) after absorption with purified complete FMDV type $C_1$.

The testing of the hexapeptide and preparation of the sera were essentially as described in Example 1.

C. Identification of virus-particle associated active element

By reasoning identical to that used in Example 1 it is concluded that the hexapeptide Asp-Leu-Ala-His-Leu-Thr (D—L—A—H—L—T) is the principal locus for the antigenic determinant of the C-type of FMDV.

These results clearly show the potential of a systematic scanning of a polypeptide sequence. They point out the likely location of the active determinant encompassed within the peptide with which Bittle, J. L. et al, Nature 298, 30–33 (1982), obtained the successful protection in guinea pigs to a subsequent challenge by FMDV.

It will, of course, be recognised that many variations and modifications may be made to the detailed description of the method of the present invention given above without departing from the method of the invention as broadly described herein.

I claim:

1. A method of detecting or determining a peptide comprising a sequence of amino acids which is antigenically active within a known amino acid sequence of an antigenic protein or portion thereof, the method comprising the steps of:
    (A). synthesizing a plurality of peptides, wherein each of said peptides is coupled to a solid phase and said plurality of peptides is arranged in an array, each of said peptides comprising a sequence of five to nine amino acids which corresponds to a sequence within the known amino acid sequence, and the peptides having overlapping amino acid sequences, said overlapping amino acid sequences comprising an overlap of one to four amino acids;
    (B). contacting said array of said peptides with antibody against the protein or portion thereof; and
    (C). detecting or determining the presence or absence of an antigen-antibody reaction between each of said peptides and said antibody to indicate whether said peptide has antigenic activity.

2. A method of detecting or determining a peptide comprising a sequence of amino acids which is antigenically active within a known amino acid sequence of an antigenic protein or portion thereof, the method comprising the steps of:
    (A). synthesizing a plurality of peptides, wherein each of said peptides is coupled to a solid phase and said plurality of peptides is arranged in an array, each of said peptides comprising a sequence of five to nine amino acids which corresponds to a sequence within the known amino acid sequence, and adjacent peptides of said plurality of peptides having overlapping amino acid sequences, whereby one peptide is related to its adjacent peptide in that from one to four amino acids at one end of the sequence of said one peptide are omitted from the corresponding end of the sequence of the adjacent peptide, and a corresponding number of amino acids is added to the opposite end of the latter sequence, with the remaining amino acids being common to both sequences;
    (B). contacting said array of said peptides with antibody against the protein or portion thereof; and
    (C). detecting or determining the presence or absence of an antigen-antibody reaction between each of said peptides and said antibody to indicate whether said peptide has antigenic activity.

3. A method according to claim 1, wherein the sequence of each of the peptides in said plurality of peptides overlaps the sequence of another peptide in the plurality of peptides by one amino acid.

4. A method according to claim 1, wherein each of said plurality of peptides is a sequence of six amino acids.

5. A method according to claim 1, wherein each of said plurality of peptides is synthesised on a solid phase carrier, and subsequent steps of the method are carried out with each peptide remaining coupled to said solid-phase carrier.

6. A method according to claim 5, wherein said solid phase carrier is a solid polymer pin or rod.

7. A method according to claim 4 or claim 5, wherein said solid phase carrier is a polymeric material selected from the group consisting of polyethylene and polypropylene, having graft-polymerised thereto a vinyl monomer containing at least one functional group to produce polymeric side-chains on the carrier.

8. A systematic array of overlapping peptides of at least five amino acids on a solid phase, wherein said peptides are covalently bound to the solid phase, wherein each peptide has a sequence corresponding to a sequence of an antigenic protein or designated portion thereof, wherein the number of overlapping peptides is sufficient to represent the sequence of the entire antigenic protein or designated portion thereof, and wherein the number of amino acids in common between two overlapping peptides is one to one less than the number of amino acids in said peptides.

9. The array of claim 8, wherein said peptides are of five to nine amino acids.

10. The array of claim 8, wherein said peptides are of six to eight amino acids.

11. The array of claim 8, wherein the number of amino acids in common between two overlapping peptides is one less than the number of amino acids in said peptides.

* * * * *